(12) United States Patent
Strausser et al.

(10) Patent No.: US 10,179,079 B2
(45) Date of Patent: Jan. 15, 2019

(54) HUMAN MACHINE INTERFACE FOR LOWER EXTREMITY ORTHOTICS

(71) Applicant: Ekso Bionics, Inc., Richmond, CA (US)

(72) Inventors: Katherine Strausser, Berkeley, CA (US); Adam Zoss, Berkeley, CA (US); James Alexander Stryker, Mountain View, CA (US); Kurt Reed Amundson, Berkeley, CA (US)

(73) Assignee: Ekso Bionics, Inc., Richmond, CA (US)

( * ) Notice: Subject to any disclaimer, the term of this patent is extended or adjusted under 35 U.S.C. 154(b) by 953 days.

(21) Appl. No.: 14/387,093

(22) PCT Filed: Mar. 22, 2013

(86) PCT No.: PCT/US2013/033472
§ 371 (c)(1),
(2) Date: Sep. 22, 2014

(87) PCT Pub. No.: WO2013/142777
PCT Pub. Date: Sep. 26, 2013

(65) Prior Publication Data
US 2015/0045703 A1 Feb. 12, 2015

Related U.S. Application Data

(60) Provisional application No. 61/614,255, filed on Mar. 22, 2012, provisional application No. 61/615,584, filed on Mar. 26, 2012.

(51) Int. Cl.
*A61H 3/00* (2006.01)
*A61H 1/02* (2006.01)
(Continued)

(52) U.S. Cl.
CPC ............... *A61H 3/00* (2013.01); *A61B 5/112* (2013.01); *A61H 1/0255* (2013.01);
(Continued)

(58) Field of Classification Search
CPC ............................. A61H 3/00–3/008; A61H 2003/001–2003/007; A61H 2201/5069;
(Continued)

(56) References Cited

U.S. PATENT DOCUMENTS 8,070,700 B2    12/2011    Kazerooni et al.
8,096,965 B2    1/2012    Goffer et al.
(Continued)

FOREIGN PATENT DOCUMENTS

JP    2010148637    7/2010
JP    2010148759    7/2010

OTHER PUBLICATIONS

Qunitero et al., "*Control and Implementation of a Powered Lower Limb Orthosis to Aid Walking in Paraplegic Individuals*", 2011 IEEE International Conference on Rehabilitation Robotics, Switzerland, Jun. 29-Jul. 1, 2011.

*Primary Examiner* — Timothy Stanis
(74) *Attorney, Agent, or Firm* — Diederiks & Whitelaw, PLC

(57) ABSTRACT

A lower extremity orthotic control system determines a movement desired by a user, particularly with a user employing gestures or other signals to convey or express their intent to the system, and automatically regulates the sequential operation of powered lower extremity orthotic components. In a particular application, the orientation of a stance leg is used to determine when the user wants to initiate a step, as well as when the user is in a safe position from which to take a step. The invention has particular applicability for use in enabling a paraplegic user to walk (Continued)

through a controlled operation of a human exoskeleton coupled to the user's lower limbs. A controller receives inputs regarding a motion desired by the user, determines the desired motion and then controls the movement of the user's legs or limbs through actuation of the exoskeleton.

15 Claims, 14 Drawing Sheets

(51) Int. Cl.
    *A61B 5/11*     (2006.01)
    *G09B 19/00*     (2006.01)
    *A61H 3/02*     (2006.01)

(52) U.S. Cl.
    CPC .. *G09B 19/0038* (2013.01); *A61B 2562/0219* (2013.01); *A61B 2562/0223* (2013.01); *A61B 2562/0247* (2013.01); *A61H 3/02* (2013.01); *A61H 2201/163* (2013.01); *A61H 2201/165* (2013.01); *A61H 2201/1616* (2013.01); *A61H 2201/1642* (2013.01); *A61H 2201/5007* (2013.01); *A61H 2201/5025* (2013.01); *A61H 2201/5028* (2013.01); *A61H 2201/5061* (2013.01); *A61H 2201/5064* (2013.01); *A61H 2201/5069* (2013.01); *A61H 2201/5079* (2013.01); *A61H 2201/5084* (2013.01); *G05B 2219/40305* (2013.01)

(58) Field of Classification Search
    CPC .... A61H 2201/5028; A61H 2201/5064; A61H 2201/163; G05B 2219/40305; A61B 5/112

See application file for complete search history.

(56) References Cited

U.S. PATENT DOCUMENTS

| | | | |
|---|---|---|---|
| 8,142,370 B2 | 3/2012 | Weinberg et al. | |
| 8,142,371 B2 | 3/2012 | Ikeuchi et al. | |
| 8,171,570 B2 | 5/2012 | Adarraga | |
| 8,366,788 B2 | 2/2013 | Moser et al. | |
| 2007/0050045 A1* | 3/2007 | Clausen | A61F 2/66 623/24 |
| 2007/0123997 A1* | 5/2007 | Herr | A61F 2/60 623/27 |
| 2008/0234113 A1 | 9/2008 | Einav | |
| 2009/0062698 A1 | 3/2009 | Einav et al. | |
| 2010/0094188 A1 | 4/2010 | Goffer et al. | |
| 2010/0114329 A1 | 5/2010 | Casler et al. | |
| 2010/0125229 A1 | 5/2010 | Rudolph et al. | |
| 2010/0179668 A1 | 7/2010 | Herr et al. | |
| 2011/0040216 A1 | 2/2011 | Herr et al. | |
| 2011/0066088 A1 | 3/2011 | Little et al. | |
| 2011/0082566 A1* | 4/2011 | Herr | A61F 2/60 623/24 |
| 2011/0105966 A1* | 5/2011 | Kazerooni | A61H 3/008 601/35 |
| 2011/0270146 A1 | 11/2011 | Chang et al. | |
| 2012/0172770 A1* | 7/2012 | Almesfer | B25J 9/0006 601/35 |
| 2013/0197408 A1* | 8/2013 | Goldfarb | A61F 5/0102 601/35 |

\* cited by examiner

HUMAN MACHINE INTERFACE FOR LOWER EXTREMITY ORTHOTICS

CROSS-REFERENCE TO RELATED APPLICATIONS

This application represents a National Stage application of PCT/US2013/033472 entitled "Human Machine Interface for Lower Extremity Orthotics" filed Mar. 22, 2013, which claims the benefit of U.S. Provisional Application Ser. No. 61/614,255 filed Mar. 22, 2012 and U.S. Provisional Application Ser. No. 61/615,584 filed Mar. 26, 2012.

BACKGROUND OF THE INVENTION

Powered lower extremity orthotic devices are being developed in the medical field to allow people with mobility disorders to walk. The device must determine when the user wants to initiate a step by some intelligent method. Many powered orthotic devices currently use a button input or follow the motion initiated by a user who is capable of moving their own leg. However, in the case of exoskeletons for paralyzed individuals, they are unable to initiate the motion independently. Furthermore, their hands may be unable to push buttons due to holding crutches, a walker, or other support device. Therefore, there is a need for a Human Machine Interface (HMI) which interprets natural user motion into actions taken by the powered orthotic. The methods of step initiation and step initiation training disclosed here were developed to give the user of powered orthotic devices independence while safely initiating a step.

SUMMARY OF THE INVENTION

The present invention is directed to a system and method by which a lower extremity orthotic control system determines a movement desired by a user and automatically regulates the sequential operation of powered lower extremity orthotic components, particularly with a user employing gestures of their upper body or other signals to convey or express their intent to the system. This is done in order to enable people with mobility disorders to walk, as well as perform other common mobility tasks which involve leg movements. The invention has particular applicability for use in enabling a paraplegic to walk through the controlled operation of a human exoskeleton in reproducing a natural human motion.

In accordance with the invention, there are various ways in which a user can convey or input desired motions for their legs by steering their leg that is in a stance phase. A control system is provided to watch for these inputs, determine the desired motion and then control the movement of the user's legs through actuation of an exoskeleton coupled to the user's lower limbs. Some embodiments involve monitoring the angle of the lower leg, particularly the shank, in order to determine the movements desired by the user. For instance, changes in shank movement are measured, such as changes in shank angle, angular velocity, and absolute positions. These embodiments are not intuitive; it is not obvious that the intention of the user can be determined from the motion of their legs when their legs are coupled to an exoskeleton. However, it is evident from basic mechanics that when a pilot shifts the device, by pushing with their crutches, for example, this force will produce motion, especially about the lower limbs of the device. In other embodiments where the device is stiff (either though mechanics or active control) these forces can still be observed in the lower limbs and these forces can be used to sense intent. In yet further embodiments, it may be sufficient to observe the movement of a distribution of forces across a foot; for instance the ratio of a force sensor at the toe and another at the heel can provide such information. Additional embodiments include designs for novel sensor systems uniquely suited to exoskeleton application.

In general, disclosed here is a system which determines the desired movement and automatically regulates the sequential operation of powered lower extremity orthotic components by keeping track of the current and past states of the system and making decisions about which new state is desired using various rules. However, additional objects features and advantages of the invention will become more readily apparent from the following detailed description of various preferred embodiments when taken in conjunction with the drawings wherein like reference numerals refer to corresponding parts in the several views.

DETAILED DESCRIPTION OF THE INVENTION

Figure 1:
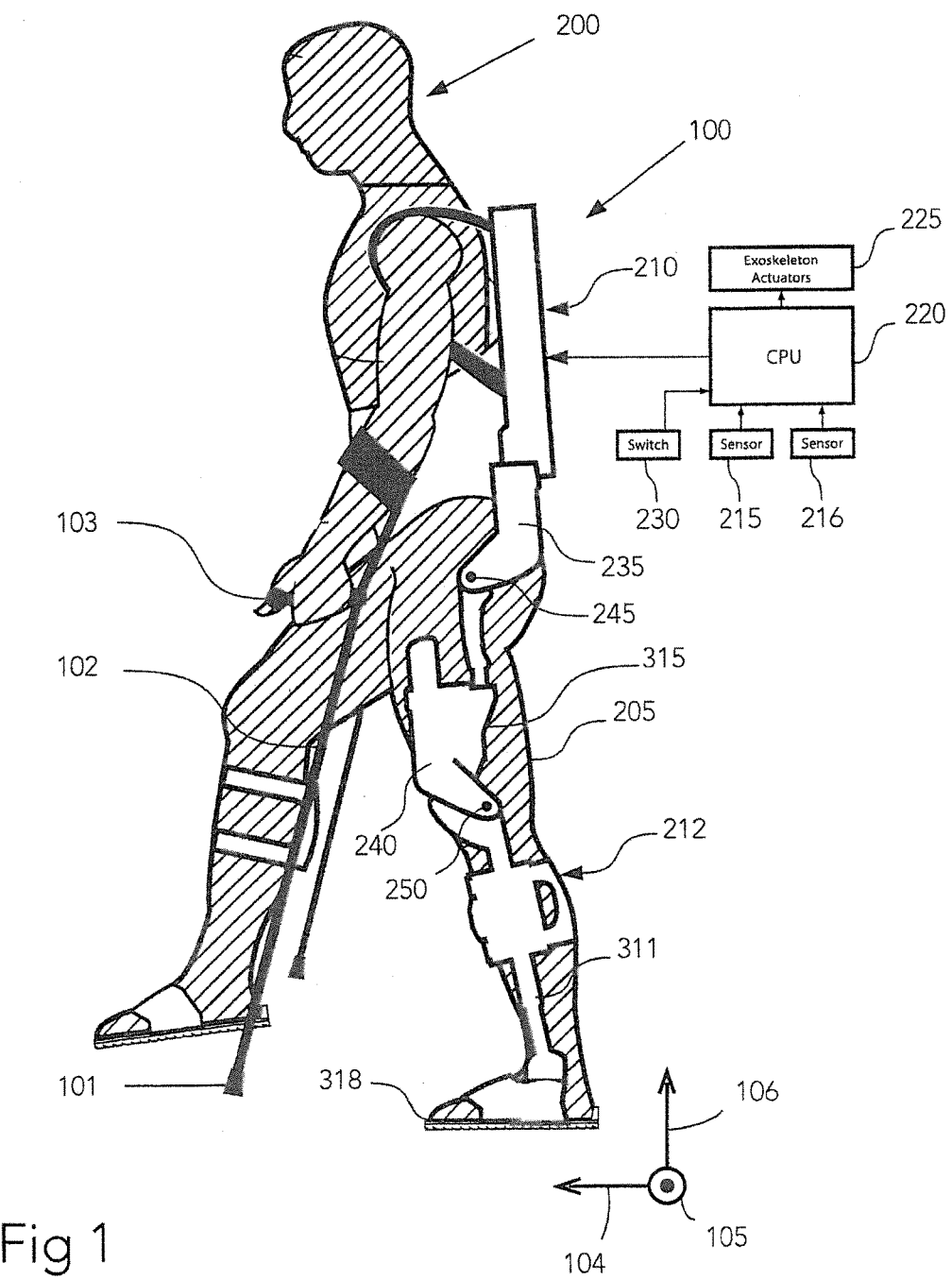
FIG. 1 is a schematic side view of a handicapped individual coupled to an exoskeleton.

This invention is used in conjunction with a powered orthotic device that provides walking motion for a user. A human exoskeleton is one example of a powered orthotic device. In FIG. 1, a powered lower extremity orthotic is shown, in this case an exoskeleton 100 having a waist or trunk portion 210 and lower leg supports 212 which may be used in combination with a crutch 102 having a tip 101. The user 200 is shown to have lower limbs 205. In a manner known in the art, trunk portion 210 is configurable to be coupled to an upper body (not separately labeled) of the person 200, the leg supports 212 are configurable to be coupled to the lower limbs 205 of the person 200 and actuators, generically indicated at 225 but actually interposed between portions of the leg supports 212 as well as between the leg supports 212 and trunk portion 210 in a manner widely known in the art (see actuators 235 and 240, for example), for shifting of the leg supports 212 relative to the trunk portion 210 to enable movement of the lower limbs 205 of the person 200. In some embodiments, the exoskeleton 100 may include a shank, 311 and a thigh 315 that comprise the leg supports 212.

For simplicity, leg 212 will sometimes be referred to as having a proximal end close to the torso, typically where leg 212 connects to trunk portion 210, and a distal end remote from the torso. FIG. 1 further includes a coordinate system, with vertical, forward, and lateral axes. In the course of the discussion, the principal anatomical planes will be referred to and understood in terms of these same axes:

- The Sagittal plane is the plane orthogonal to the lateral axis 105
- The Coronal plane is the plane orthogonal to the vertical axis 104
- The Frontal plane is the plane orthogonal to the forward axis 106

FIG. 1 also shows a plurality of sensors 215, 216 that can be used to establish the orientation of the exoskeleton. Orientation is understood here to include up to the position of the exoskeleton in all six spatial axes (three linear and three rotation), the relative position of the exoskeleton parts in linear and angular space, and possibly the interaction forces between linkages of the device as well as with the environment. Inertial measurement units (IMUs) could be coupled to the leg support 212. An inertial measurement unit is generally composed of an accelerometer and a gyroscope and sometimes a magnetometer as well; in many modern sensors these devices are MEMS (mico electromechanical systems) that have measurement in all three orthogonal axes on one or more microchips. The behavior of IMUs is well understood in the art (IMUs being used for applications from missile guidance to robotics to cell phones to hobbyist toys); they typically provide measurement of angular orientation with respect to gravity, as well as measurement of angular velocity with respect to earth and linear acceleration, all in three axes.

Although N+1 IMUs would be sufficient to fully define the behavior of an N degree of freedom device (depending on bandwidth requirements), it is often convenient to use sensors that measure relative motion between two rotary joints; such sensors are shown on right and left knee and hip joints 245 & 250, and include, without limitation, encoders, potentiometers, and LVDTs. These sensors can be used to determine orientation or used to determine lateral and vertical distance between joints through a geometric model. Furthermore, FIG. 1 shows an exoskeleton with feet 318 and ground contact sensors mounted between the feet and the ground (sometimes referred to as the support surface); these sensors help the exoskeleton understand when it is in contact with the ground (often referred to as the stance phase of walking), but are not strictly necessary in all embodiments. In some embodiments, these ground contact sensors may simply be binary switches 230, in other embodiments they may be force sensors capable of resolving the force acting on the foot, and in yet other embodiments, they may resolve the distribution of the force, as well as the level of the force, across the foot.

In some embodiments, it may be desired to estimate the velocity of the person, the exoskeleton, or some part thereof. In general, there are some types of sensors that produce velocity readings directly, such as tachometers and the gyroscopes mentioned above. It is also possible to directly differentiate the change in a position sensor reading or in a position estimated from multiple sensors if the position measurement has sufficient resolution or the bandwidth of the resulting velocity measurement is sufficiently slow. Once local rotational velocities are established, they may be geometrically added to derive the angular velocity of the next link in the kinematic chain or they may be resolved to linear velocities if the position about which the rotation occurs is known (for example, the linear velocity of a knee joint may be derived from the shank angular velocity if a foot is known to be planted on the ground). If the angular orientation of the link is also known with respect to gravity, the velocity may be resolved into vertical and horizontal components. These techniques are well understood in the art and are repeated here only for reference.

This invention has three main aspects. The first is the ability for the user to independently initiate a step based on his lower limb angle. The second is feedback to the user and/or operator during use about the timing of the steps. These two options can be used independently or simultaneously to give feedback to the user while stepping automatically. And, the third aspect is providing the person wearing the exoskeleton or assisting with the exoskeleton the ability to manually initiate a step while providing safety limits that do not allow them to initiate a step when taking a step would not be safe.

Lower Limb Orientation Based Step Initiation

For walking exoskeletons, the method to initiate an action has been the subject of numerous studies. While others have proposed torso motion, tongue motion, or sensor/gesture based systems, the underlying principle is to determine when the user desires to take a step and initiate that step. This invention utilizes the orientation of the stance leg to determine when the user wants to initiate a step as well as when the user is in a safe position from which to take a step.

Figure 2:
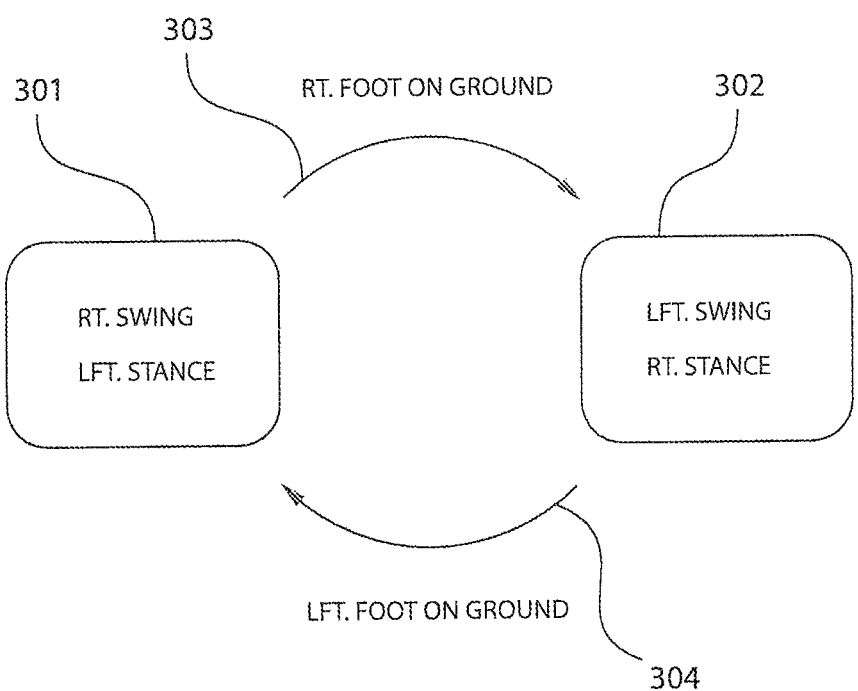
FIG. 2 schematically illustrates a simple state machine with two states.

At this point, the control implementation will be discussed in terms of a finite state machine which determines how the system will behave. The state machine of a controller 220 controls when the exoskeleton 100 switches between two states. This very simple state machine is illustrated in FIG. 2 where 301 represents the first state, 302 represents the second state, and the paths 303 and 304 represent transitions between those states.

Figure 3:
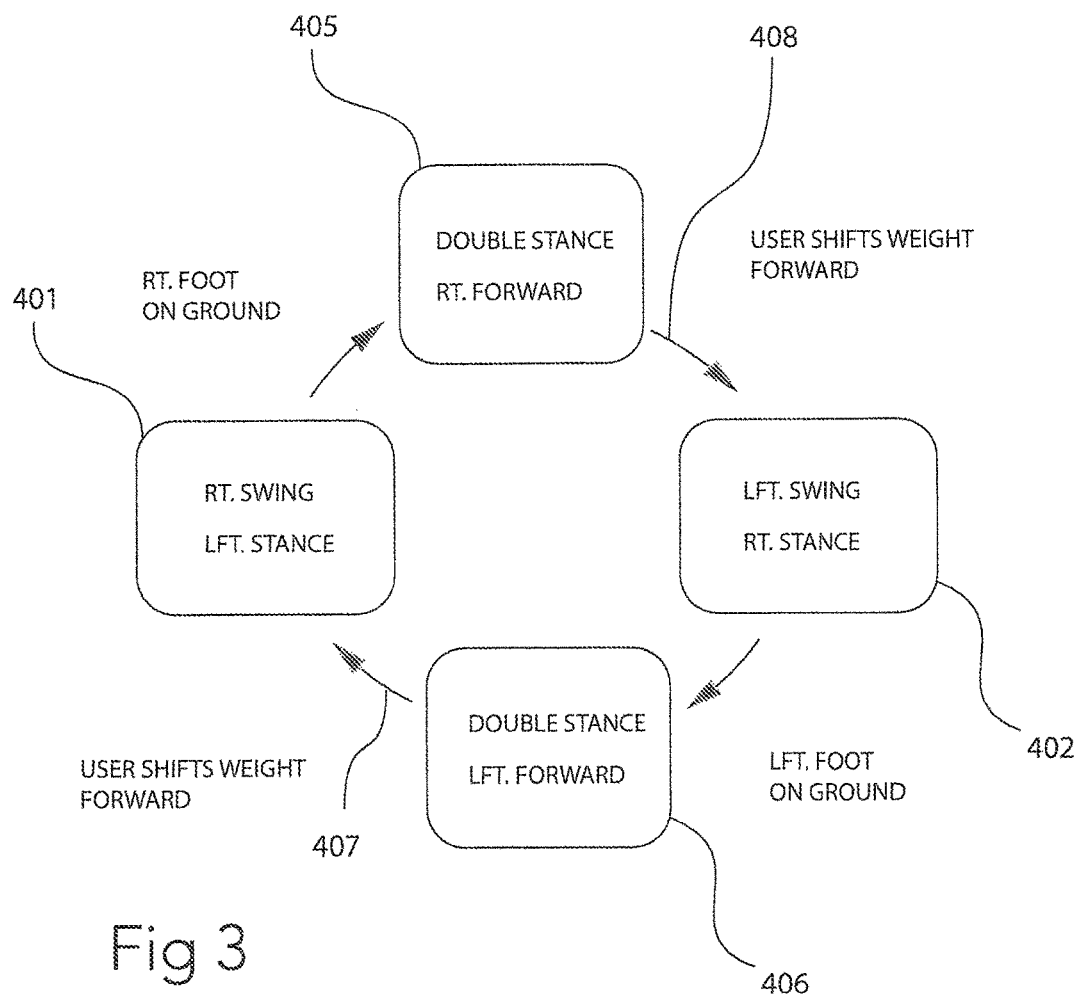
FIG. 3 schematically illustrates a state machine with more states.
Figure 4:
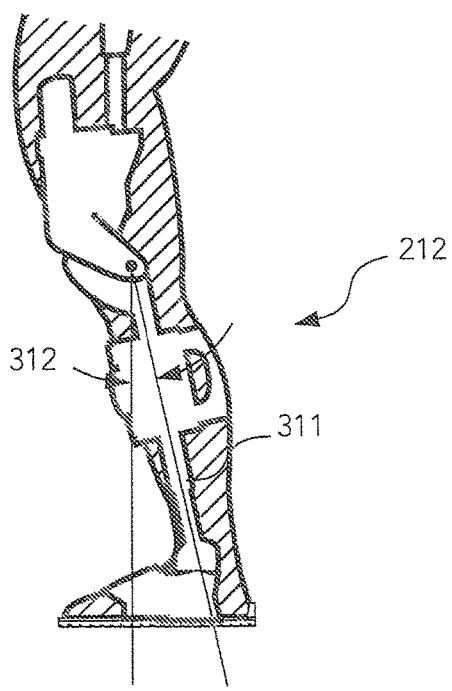
FIG. 4 illustrates the angular orientation convention of the shank.

Further embodiments of the state machine allow for walking to be divided into more states. One such arrangement employs adding two double stance states as shown in FIG. 3. These states are indicated at 405 and 406 and occur when both feet are on the ground and the two states distinguish which leg is in front. Furthermore, the state machine, as shown in FIG. 4, adds user input in the form of crutch orientation. In this embodiment, the right and left swing states 401 and 402 are only entered when the user has indicated they would like to take a step, as represented by transitions 407 and 408 respectively. It is important to note that the left and right leg can use independent state machines that check the other leg state as part of their conditions to transition between states for safety. This would produce the same results as the single state machine.

For clarity, a typical gait cycle incorporates of the following steps. Starting in state 405, the user moves forward over the right leg and triggers transition 408 by the methods below. Thereafter, state 402 is entered wherein the left leg is swung forward. When the left leg contacts the ground, state 406 is entered. During state 406, the machine may make some motion with both feet on the ground to preserve forward momentum. Then, the user indicates a transition to take a right step 407 by the methods below. Then the machine enters state 401 and swings the right leg forward. When the right leg contacts the ground, the machine enters state 405. Continuing this pattern results in forward locomotion. Obviously, an analogous state machine may enable backwards locomotion by reversing the direction of the swing leg motions when the crutch motion direction reverses.

At this point, is should be noted that the stance phases may be divided into two or more states, such as a state encompassing heel strike and early stance and a state encompassing late stance and push off. Furthermore, each of these states may have sub-states, such as flexion and extension as part of an overall swing.

Using a program that operates like a state machine has important effects on the safety of the device when used by a paraplegic, because it insures that the device proceeds from one safe state to another by waiting for appropriate input from the user to change the state, and then only transitioning to an appropriate state which is a small subset of all of the states that the machine has or that a user might try to request. This greatly reduces the number of possible state transitions that can be made and makes the behavior more deterministic. For example, if the system has one foot swinging forward (such as in state 401 of FIG. 3), the system is looking for inputs that will tell it when to stop moving that foot forward (and transition to a double stance state such as 405) rather than looking or accepting inputs that would tell it to lift the other foot (such as moving directly to state 402).

From any state, the user or operator can indicate the desire to go back to a standing still state. This straightens both legs and holds the torso upright. This state can be the precursor to sitting or can simply be used to rest or reposition.

Shank Angle Orientation

It was found that one reliable indication of a desired step was the shank angle of the forward leg during double stance with respect to the ground. FIG. 4 shows a leg support 212 of a human exoskeleton 100 with a leg support shank 311. The leg support shank angle with respect to the gravity vector is indicated at 312.

The shank angle is a consistent indicator of when the user is prepared to take a step; therefore, in one embodiment of the invention, when the leg support shank 301 of the forward leg (during double stance) is leaned forward sufficiently, this indicates the desire to take a step and the powered orthotics controller initiates a step. One skilled in the art will note that there are many ways to measure the leg support shank angle with respect to the ground. One example is an exoskeleton shank 301 with an Inertial Measurement Unit (IMU) installed within it. In this case, this leg support shank IMU would be the sensor 215 shown in FIG. 1 and it would provide a signal to the controller 220. When the leg support shank angle 312 reaches a predetermined angle, controller 220 would direct the actuators 225 to make a forward step with the trailing leg support (that is, the other leg support).

Figure 6:
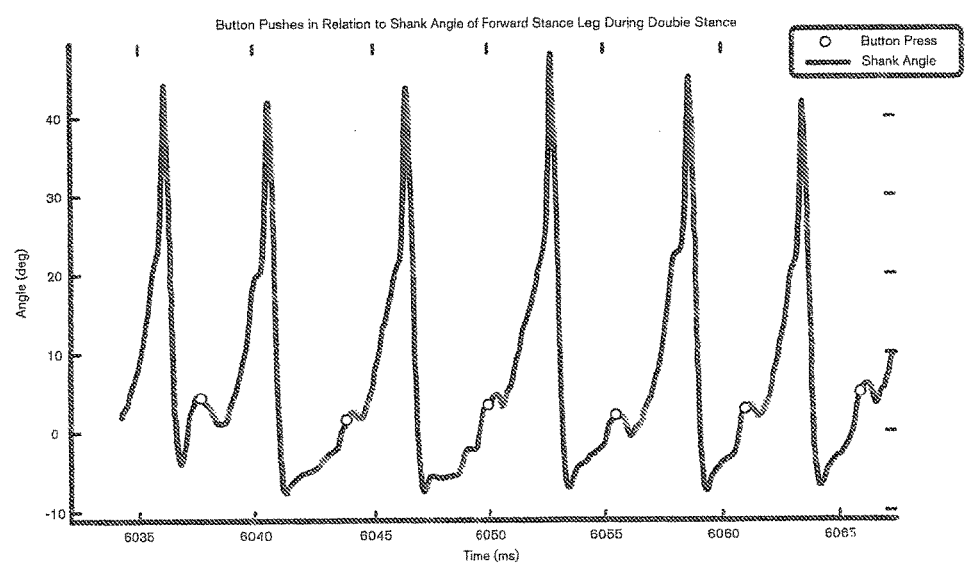
FIG. 6 represents experimental data gathered from the invention.

FIG. 6 shows an example of data comparing the angle of the shank to manual step initiation by a skilled operator of the device. It is clear from the data that the shank angle is a repeatable metric to indicate when the device should trigger a step.

In another embodiment where the device legs reach the ground, an IMU is not used, but instead an angle measurement sensor is placed on the ankle of the device. In this embodiment, the angle sensor could be an encoder, a potentiometer, or any of a number of angular displacement sensors that are well known in the art. The controller then uses the ankle angle to estimate the angle of the shank with respect to the local terrain. The average local angle of the ground with respect to horizontal is often referred to as the slope of the terrain or the slope of the ground (in many cases, such as wheelchair ramps, the slope may be constant over the entire surface). In the event that the slope is zero (i.e., the ground is flat), this embodiment will result in the same step initiation as the IMU based embodiment. When, however, the slope is not zero, the controller may be required to estimate and correct for the change in the ankle angle measurement due to the slope. In some embodiments, the estimate of the slope may also be used to modify the device behavior. As an extension of this embodiment, the device may better estimate the true shank angle if ground contact sensors are used to determine that the foot is flat when the ankle angle is recorded.

Another example of a method of determining the leg support shank angle is to have an IMU installed onto another link on the device, and to have sensors which measure the joint angles between the links. The IMU can then be used to determine the orientation with respect to gravity of the link in which it is installed. Then the leg support shank angle 302 can be calculated using the known joint angles which are between the shank link 301 and the link with the IMU. A number of other ways (besides IMUs) to measure angles with respect to gravity exist and could also be employed.

This embodiment of the invention discussed so far works most reliably if the knee flexion angle is small. A second embodiment considers only the thigh angle of the stance leg (forward leg during double stance) to determine that the user is indicating a forward step is desired. In a similar manner, a threshold is set for the thigh angle that determines that the person is shifted forward and prepared to take a step.

A third embodiment is to consider the line formed by the hip and ankle of the stance leg; this embodiment also helps in the event that the knee flexion angle is small. The exoskeleton will transition into a state that corresponds to taking a step (e.g., the right swing state 401 in FIG. 3) when the angle of the line exceeds a threshold. Equivalently, the exoskeleton controller may decompose the hip-ankle line into a forward and a lateral component and only transition to stepping when the forward component and the lateral component exceed respective thresholds.

These additional embodiments can all be accomplished by utilizing the global position of the joint as well. The hip joint location can be calculated to determine the forward position of the hip. The knee position can be calculated to determine if the knee is forward.

In any of these embodiments, the angle threshold of the leg may be determined by a fixed angle or may be dependent on the velocity of the walking. This allows the step motion to be anticipated in faster walking thus taking into account the momentum of the user. A user will be able to initiate a step when their weight is further back if their momentum is sufficient to propel them forward over the stance leg. The velocity can be judged on over ground walk speed or the velocity of the stance leg.

In conjunction with any of these embodiments or independently, the user's weight shift forward can be measured through pressure or reaction forces. In one embodiment, the sensor measuring foot pressure or ground reaction force under the foot can also be used to determine when the user's leg has been weighted. This measurement can be used independently or combined with the forward shift measurements to determine when to initiate a step. In another embodiment, the reaction force can be measured as an interaction force on the stance leg indicating that that leg is bearing weight.

Figure 7A:
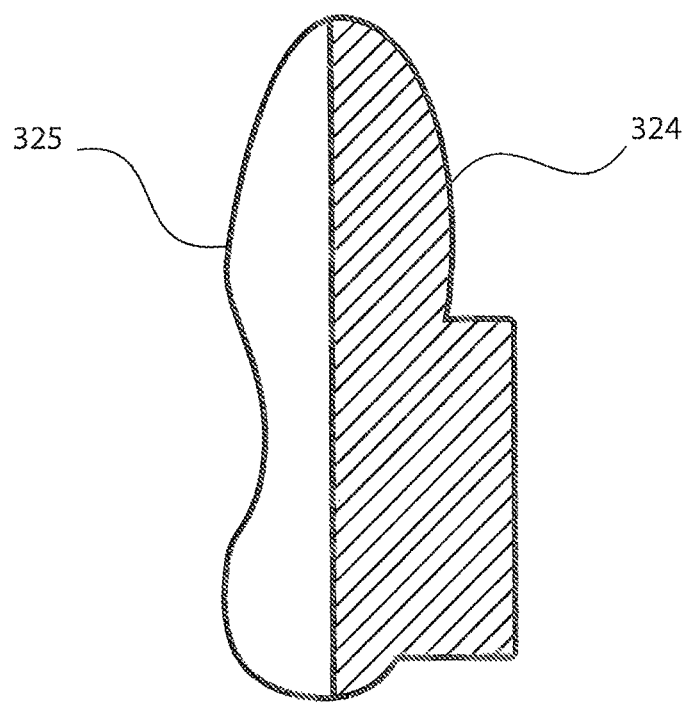
FIG. 7a schematically represents the outline of an exoskeleton foot.
Figure 7B:
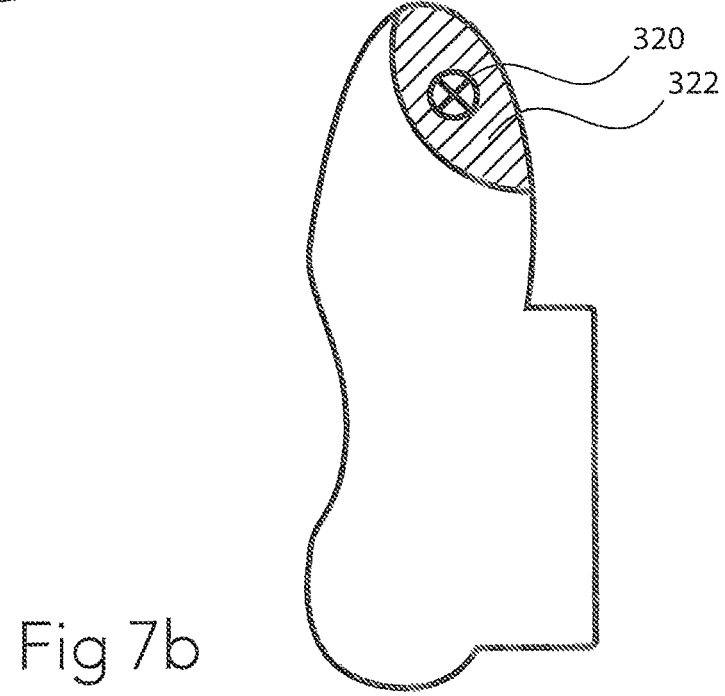
FIG. 7b schematically represents the outline of an exoskeleton foot with a force distribution.

In a further embodiment, the sensors measuring the ground reaction force resolve the geometric center of all the reaction forces under a foot in stance; this point is called the center of pressure. The controller may track this center of pressure over time to create a center of pressure trajectory and divide the stance phase into a series of states based on the progression of the center of pressure. FIG. 7b shows a center of pressure location, 320, schematically imposed on a right exoskeleton foot. The center of pressure has entered a region, 322, on the forward and lateral portion of the foot. When the controller 220 receives a signal that this has occurred, the controller will transition the other (left) leg into swing state 402 in FIG. 3. FIG. 7a illustrates the usage of the anatomical terms medial, 325, and lateral, 324, to indicate the inside and outside of the foot respectively.

In yet a further embodiment, it is possible to have a very large number of states corresponding to small changes in the center of pressure and creating ever finer motions of the other leg that is taking a step. In the limit, it is possible for the motion of the leg that is taking the step (i.e., entering the swing phase) to be a function of the center of pressure of the leg that is in stance such that there is, in effect, one state for each sampling of the center of pressure 320. In this embodiment, the person wearing the device would be able to use the crutches to push their weight forward or backward, thus moving their center of pressure and continuously controlling the motion of the stepping leg.

In conjunction with any of these embodiments, it is possible to enable operations beyond simply taking a step. For example, if a person wearing exoskeleton 100 is seated, they could signal a desire to stand by pushing with crutches or on the chair so that the orientation of shank 311 changes and enters a region corresponding to standing. As a safety measure, it may be necessary to have two states, a first state entered through an external control device to tell controller 220 to listen for the signal from the person to stand, and a second state corresponding to standing when the controller receives a shank angle that has exceeded the set threshold.

Foot Based Methods

Figure 11:
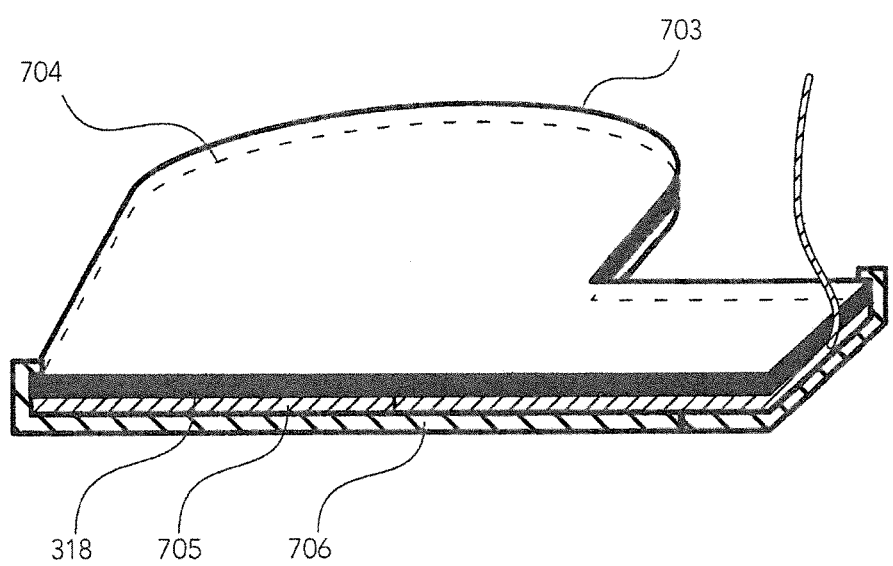
FIG. 11 is an illustration of an exoskeleton foot interfacing with an elastic housing and containing an electronic pressure sensor.

It was found that due to the high shear forces exerted on an exoskeleton foot, existing foot pressure distribution sensors are not ideally suited to the needs of an exoskeleton system. Designs were developed for the novel foot pressure sensor systems particularly suited for use with any of these embodiments. FIG. 11 shows one of these embodiments in which the foot 318 interfaces with an elastic housing 706 to enclose an electronic pressure sensor 705. It was found that in order for such a sensor to be robust against the shear forces and the impact loads of the exoskeleton application, a substantially continuous interlocking joint around both the upper side perimeter of foot 703 and lower side of the perimeter 704 must be maintained while leaving a cavity for an electronic pressure sensor 705. In this configuration, the walls of the elastic housing 706 distribute shear forces directly into the foot 318 while transmitting normal forces through the electronic pressure sensor 705 into the foot 318. This configuration works well as both pressure distribution sensors on the top and bottom side of the foot 318 allowing the controller 125 to sense person to exoskeleton interaction (if the sensor is between the person and the exoskeleton foot 318) or exoskeleton to terrain interaction (if the sensor is between the exoskeleton foot 318 and the ground).

These novel pressure distribution sensors, while highly robust can suffer from a loss of calibration due to the stresses generated by the high forces of the application. It was also observed that in this application the dynamic effects of the mass of the person's leg and the exoskeleton foot 318 are substantially negligible compared to the forces imparted onto the foot by the person, the exoskeleton, and the terrain. An additional embodiment includes three sensors, two such novel pressure distribution sensors configured to measure center of pressure on the top and bottom of the foot 318 and a torque sensor between the foot 318 and the shank 311. Torque sensors suitable for this application are well known in the art as the connection between the foot 318 and the shank 311 is a type of interface commonly found in machine design. These sensors include strain gages and prefabricated load cells and are readily available and well understood. It was discovered that when the substantially negligible dynamic effects are ignored or compensated for such an arrangement allows the controller 125 to continuously remove the bias of the pressure distribution sensors using the information from the torque sensor.

Bias adjustment is accomplished by evaluating the torques about the foot 318 in the sagittal plane from the three sources: the terrain, measured by the distance of the center of pressure location on the bottom of the foot 318 to the ankle joint axis; the person, described by the distance from the center of pressure on the top of the foot 318 to the joint axis; and the connection between the foot 318 to the shank 311, described by a torque sensor in the connection between the foot 318 and shank 311. Elementary mechanics teaches that the torque applied on the foot 318 from the terrain must equal the torque applied onto the foot 318 from the person plus the torque applied onto the foot 318 from the exoskeleton: $T_T T_P + T_E$ (again, the dynamic effects of the foot are neglected because of the relatively small mass of the foot). In this embodiment $T_T$ is measured using the pressure distribution sensor on the bottom of the foot 318, $T_P$ is measured using the pressure distribution sensor on the top of the foot 318, and $T_E$ is measured using the torque between the foot 318 and the shank 311. The equation is now over-defined and methods are readily available to a person skilled in the art to remove bias from $T_T$ and $T_P$ using the more accurate sensor $T_E$.

An additional embodiment of this technique is used to reduce complexity or improve robustness rather than improve performance by using any combination of only two of the sensor systems for $T_T$, $T_P$, and $T_E$. Using the same equation, $T_T = T_P + T_E$, the value of the missing sensor can be estimated directly. This is of particular interest for estimating $T_T$ when only using $T_P$ and $T_E$. Obviously, in this embodiment, any bias between the pressure distribution sensors cannot be removed, but this may be acceptable, particularly in applications where the terrain is rough and installing pressure sensor 705 below foot 318 may expose it to damage.

As an extension to this embodiment, if the torque sensor is configured as a two axis force sensor, the same torque balance equation presented above may be applied about axis 104 as well as axis 105 so that moments in the frontal plane may be estimated or corrected as well as those in the sagittal plane. Furthermore, if the torque sensor is also configured to measure force along axis 106, the forces may be summed as $F_T = F_P + F_E$, providing a way to correct between sensors or use two sensors to construct all three measurement.

Figure 12A:
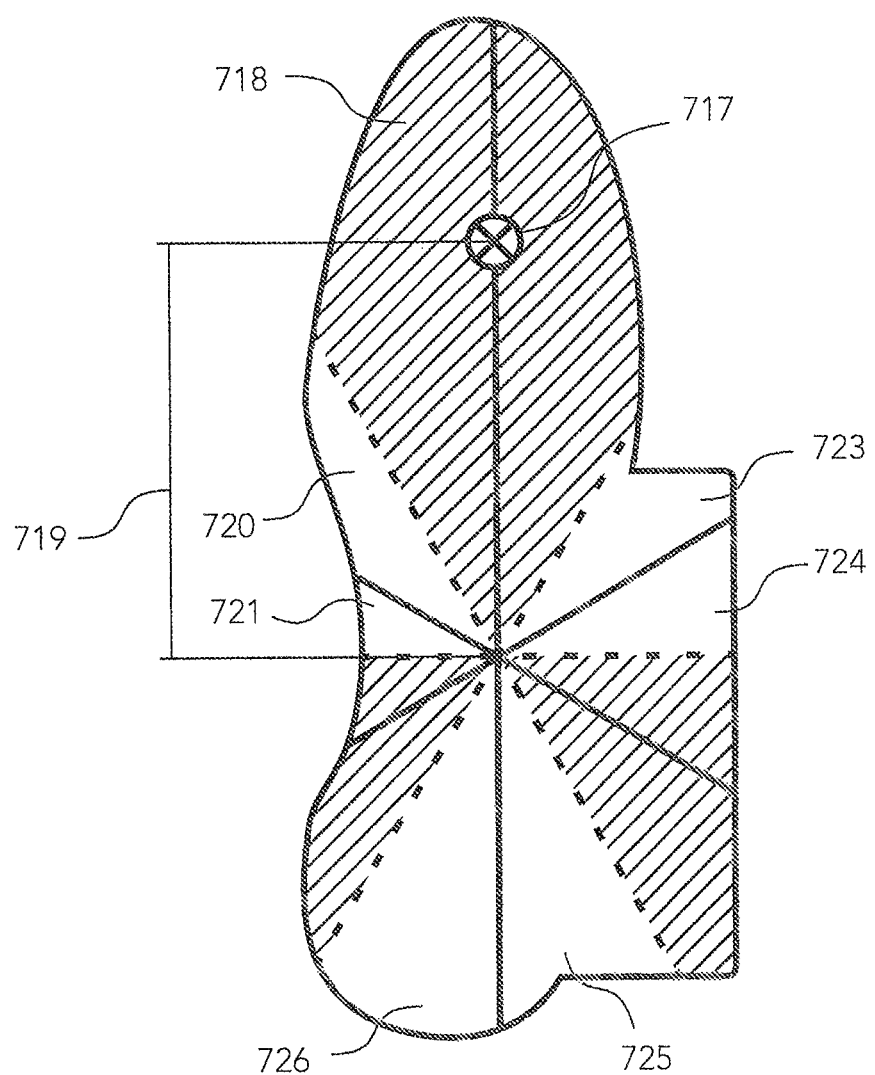
FIG. 12a schematically represents the outline of an exoskeleton foot with a novel center of pressure and force sensor.
Figure 12B:
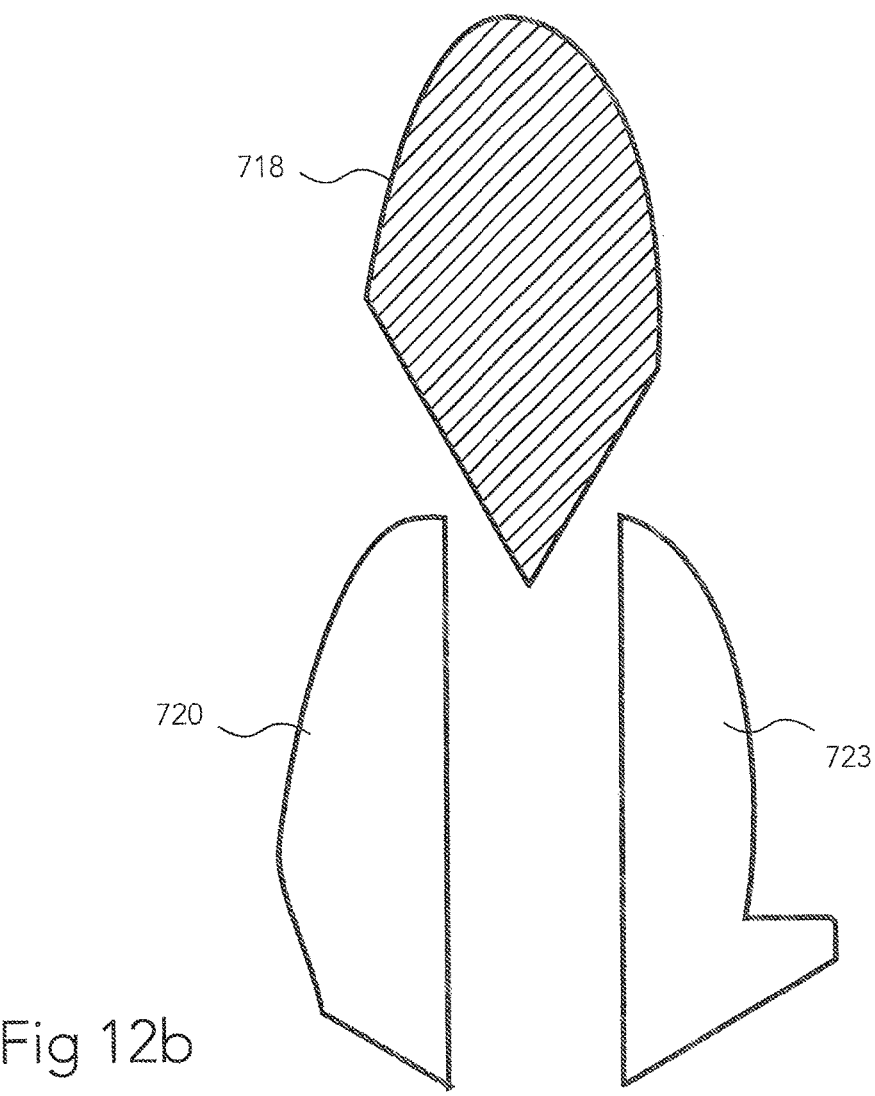
FIG. 12b schematically represents two electrodes from FIG. 12a and the sensitivity region between them.

In yet a further embodiment, FIG. 12a shows a novel architecture for an electronic pressure sensor 705 suitable for determining center of pressure location. This novel electronic pressure sensor is comprised of two sets of three electrodes (electrode 1A 720, electrode 1B 724, electrode 1C 726, electrode 2A 723, electrode 2B 725 and electrode 2C 721) placed entirely on one side of a piezoresistive material or layer. The resistance of the piezoresistive material is locally reduced when pressure is applied to the material. By applying a voltage potential between the two sets of electrodes, controller 125 can measure the change in resistance can be measured electrically through techniques well understood in the art. A given pair of electrodes can measure the resistance in the sensitivity region for those electrodes. It should be understood that the sensitivity region is approximate and heavily dependent on the chosen geometry, but may be characterized experimentally. FIG. 12*b* shows a detail of two electrodes 720 and 723 and their corresponding sensitivity region 718. The centroid, 717, of the sensitivity region can be calculated geometrically and is readily apparent to a person skilled in the art. By measuring the distance between the origin and the region centroid 719 and measuring the average pressure in a region for each sensitivity region both the normal force and center of pressure location can be determined while the unwanted shear forces are substantially rejected. The equation used to make this determination for a system with n regions is:

$$CP \text{ in the forward axis } 104 = \sum_{1}^{n} \frac{\text{Region Average Pressure} * \text{forward distance from origin to region centroid} * \text{Region Area}}{\sum_{1}^{n} \text{Reigion Average Pressure} * \text{Region Area}}$$

$$CP \text{ in the latteral axis } 105 = \sum_{1}^{n} \frac{\text{Region Average Pressure} * \text{lateral distance from origin to region centroid} * \text{Region Area}}{\sum_{1}^{n} \text{Reigion Average Pressure} * \text{Region Area}}$$

Force in the normal vertical axis 106 =

$$\sum_{1}^{n} \text{Region Average Pressure} * \text{Region Area}$$

This novel architecture for a force distribution sensor allows a highly robust yet low profile sensor to be constructed with little susceptibility to shear. Additionally, all of the electrodes (720, 721, 722, 723, 724, 725, 726) make electrical connection with the piezoresistive material on a single side which greatly simplifies the construction and allows a single printed circuit board to include all electrodes. There is no other sensor technology currently available to the art that can withstand the loads required in the exoskeleton application, fit into a small form factor of as little as two 0.031 inch (0.08 cm) thick layers, and provide simultaneously center of pressure location in the forward axis 104, center of pressure location in the lateral axis 105 and normal force in the vertical axis 106. When combined with previous embodiments to remove the bias common with piezoresistive materials, a high functionality, high accuracy, high robustness and low form factor pressure sensor can be constructed. Additional embodiments of this architecture can be created using additional shapes of the electrodes and the corresponding sensitivity regions 718 created between the electrodes. These embodiments are not limited to sensitivity regions 718 of equal area because the equations for the center of pressure locations and force include the areas of the sensitivity regions 718 in their calculation.

Coronal Plane Measurement

An additional indicator on an intention to take a step is a shift of the user's body away from a foot in preparation for swinging that foot. This shift can be indicated by either a shift in the center of pressure of the other foot or a shift in the position of the body. In an embodiment of the latter, the lateral shift of the user, indicated by measuring either the angle of the shank or another segment of the exoskeleton in the coronal plane indicates preparation for the next step.

Safety Checks

Before the step is initiated, the controller 220 may check other variables in order to determine that it is safe to take the step. For example, the step should not be taken if the user has fallen too far forward. Therefore, a forward threshold can be set such that the step is no longer taken if the person has progressed that far forward. In principal, this forward threshold may be set on any of the metrics (shank angle, foot center of pressure, etc.) discussed above. The result is, in effect, that the step is initiated when the metric is not simply larger than a threshold, but that it is within an acceptable range.

An additional indication that the step may not be safe is the forward velocity of the shank angle. If the leg is falling forward too quickly indicating a lack of stability, the step should not be initiated. Likewise, if the user is moving backwards (such as in the case where they are correcting having been shifted too far forward), the step should not be initiated as the momentum of the user is in the wrong direction. In some embodiments, however, a backwards motion at a low velocity may be used to trigger a backwards step.

In addition, the threshold may be adjusted based on the velocity of the shank angle. For example, if the user is moving quickly over his foot, the controller can initiate a step earlier utilizing the forward momentum to complete a safe step in time. Likewise, if the user is moving slowly, the controller will initiate the step later to ensure that the user's weight is over his foot.

Figure 8:
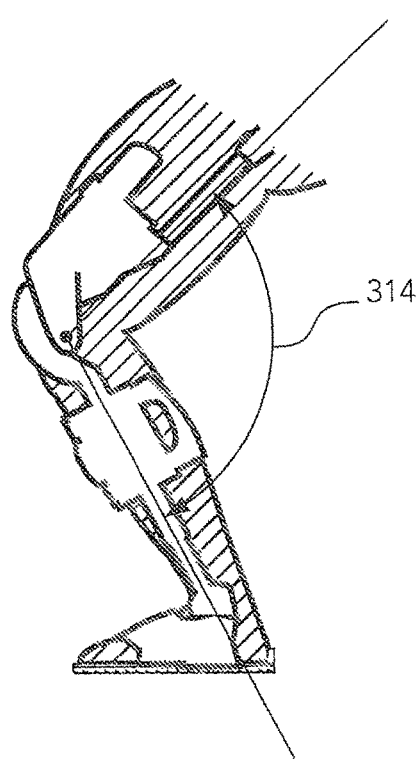
FIG. 8 is an illustration of a leg in an unsafe condition.

Sometimes a user may land on the swing leg when the swing leg is not fully extended as shown in FIG. 8. This happens when the user falls onto the leg too quickly or stubs their toe. In this case, the shank angle or ankle to hip line may be sufficiently forward, but the user is not ready for a step since the knee angle 314 is still bent. Therefore, an additional guard may be added to delay the step until the leg is sufficiently extended.

These methods could be used in conjunction with additional sensors to provide additional input. For example, crutch force sensors can be used to ensure that the crutches are planted on the ground.

The controller may also check sensors measuring pressure on the foot or ground reaction force under the foot to ensure that sufficient weight has shifted to the forward foot. This indicates that that leg is ready to accept the weight of the user and will not result in the user falling backwards.

Figure 9A:
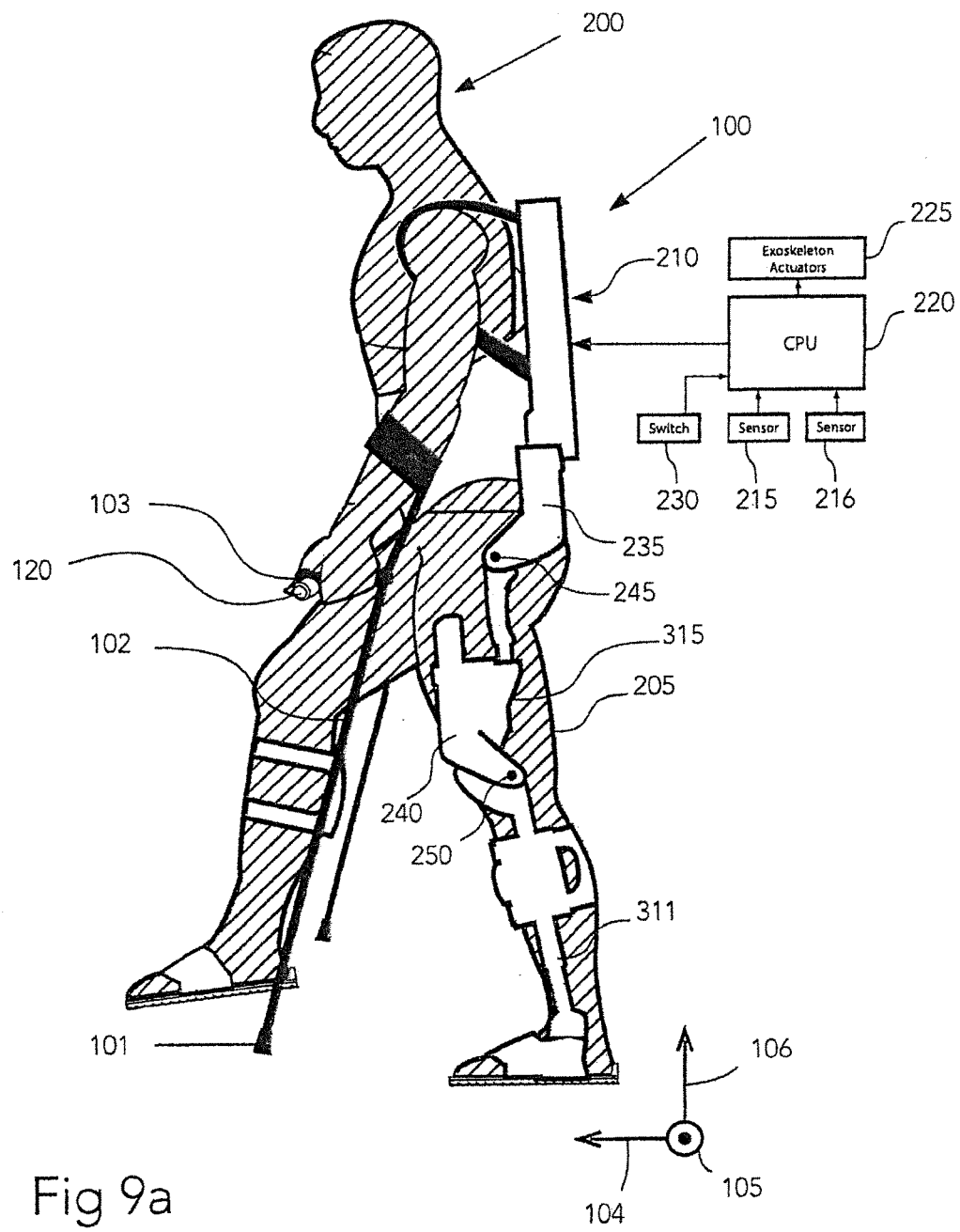
FIG. 9a is an illustration of the device user directly controlling stepping.
Figure 9B:
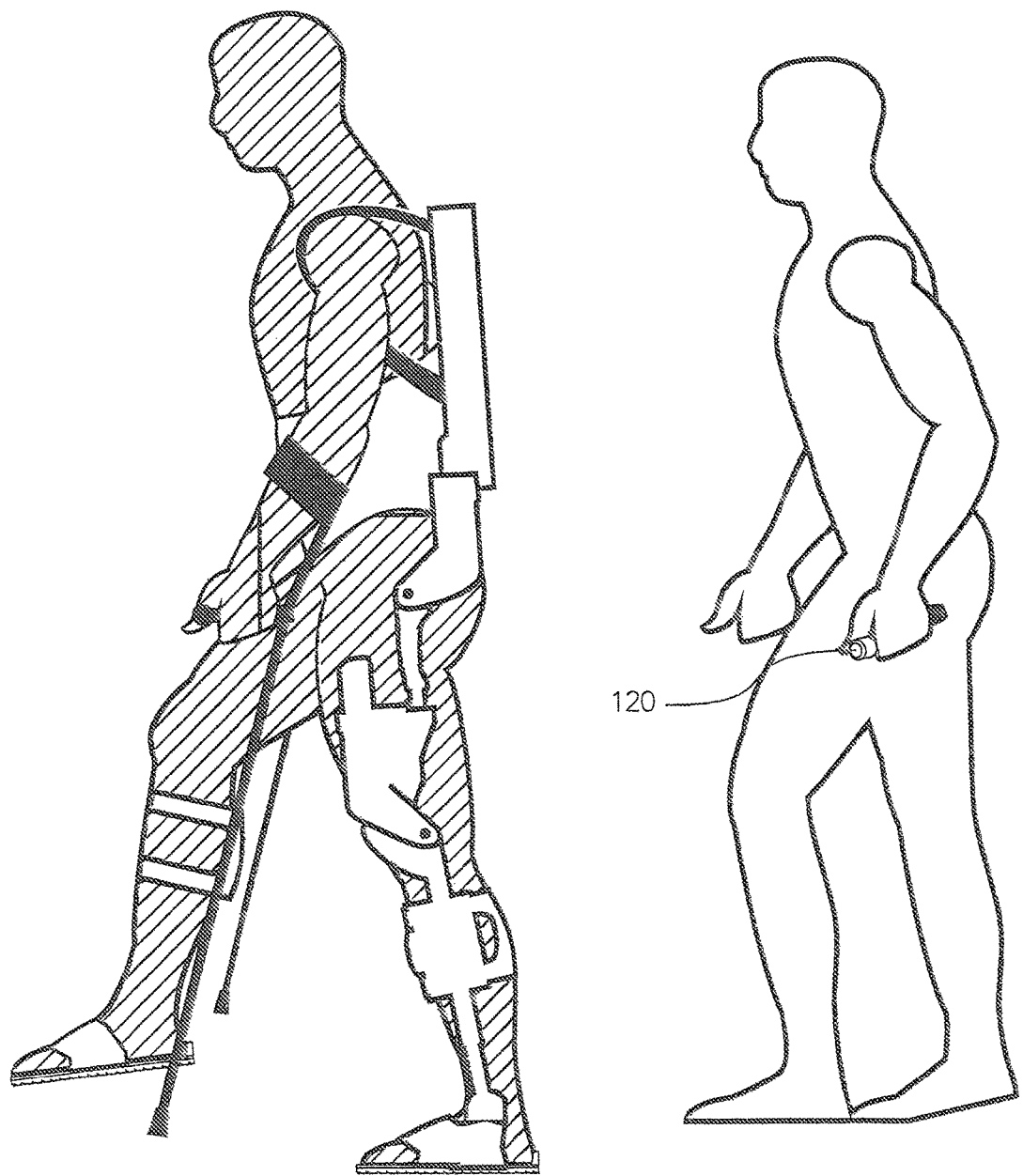
FIG. 9b is an illustration of the device operator directly controlling stepping.

In one embodiment, the exoskeleton includes two additional methods of initiating a step. The step can be initiated by an input, such as a button press, given by the person wearing the device. In this embodiment, shown in FIG. 9*a*, the button, 120, must be in a location that the user can press every step, such as on their crutch, 103. The step can also be initiated by an input, such as a button press, given by the operator, as shown in FIG. 9*b*; in this embodiment button 120 will not be connected to the crutch so that instead the operator can hold it. In this embodiment, the operator is a second person who operates the device so that the person wearing it does not need to be as experienced in the operation of the device.

Terminating a Step

In some cases, a step may be initiated in an unsafe configuration or the user may shift to put them in an unsafe position. In this case, the step should be terminated for safety by extending the leg to provide balance and stability. The step may be terminated if the stance leg thigh angle (or hip position) begins to travel backwards after step initiation. This is indicative of the step being taken too early and the user not progressing forward safely.

Training

This invention also provides a method for training both the user and the operator. By giving haptic, auditory or visual feedback as to when the step should be taken based on the forward shift threshold given in the above embodiments, the user/operator team can learn what a stable position looks and feels like. In this embodiment, the exoskeleton provides a beep or light (or other sensory feedback) when the step should be initiated based on given parameters (such as those described in position based step initiation). Those skilled in the art will recognize that numerous methods of feedback are possible which all accomplish indicating a stepping threshold.

This feedback can also be used as a metric for determining if a user is ready to control the exoskeleton independently. This is useful in exoskeletons which give the user (not the second individual referred to as an operator) control over taking a step by pushing a button themselves. Before a user is allowed to use such a system, the therapist must feel comfortable in their ability to determine when they are ready for the next step. The exoskeleton can utilize the "ideal" step initiation time (the one determined by the methods discussed above) and create a score based on when the user pushes the button in relation to the "ideal" trigger. When the user is getting proficient, there will be a very small time difference between the step initiation time determined by the system, and the actual time that they push the button.

Figure 10:
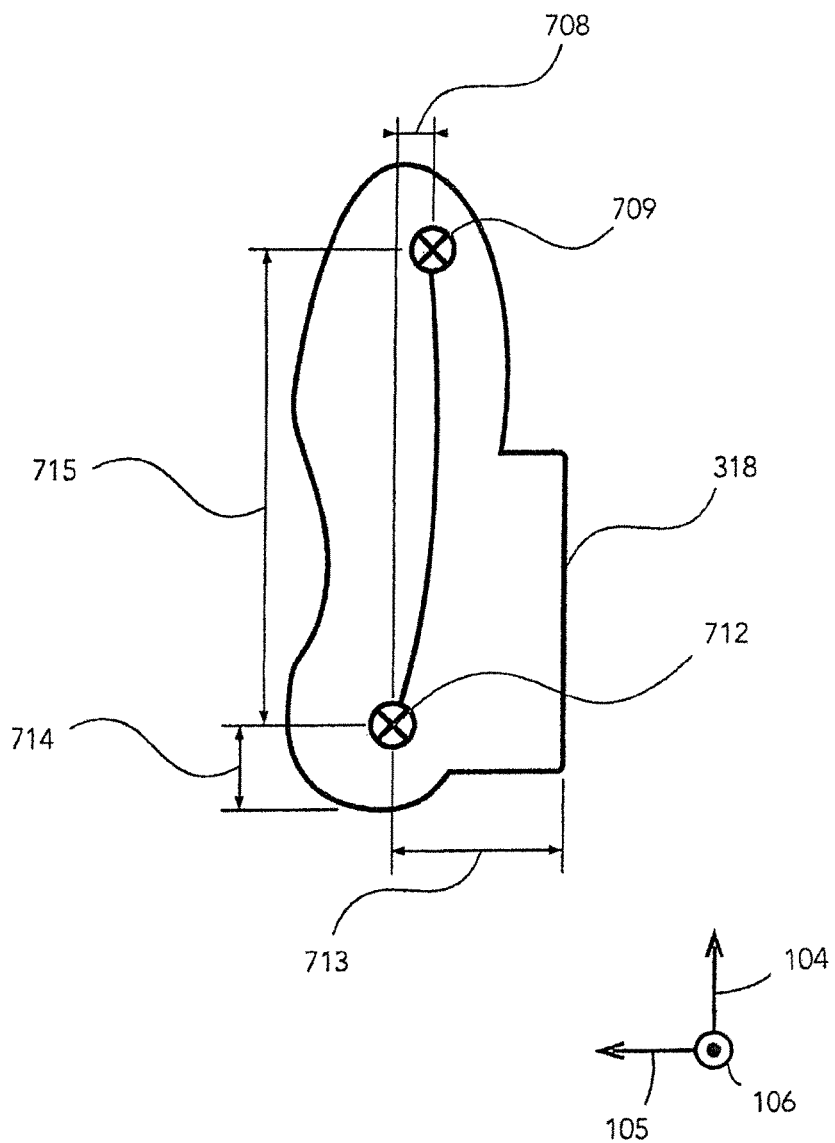
FIG. 10 schematically represents the outline of an exoskeleton foot with a moving center of pressure.

In a simple embodiment, a step can be characterized by four metrics: the horizontal and forward change 708 and 715, and the horizontal and forward offset 713 and 714 of the center of pressure 709, 712, as shown in FIG. 10. Then, these two metrics may be compared over two or more steps and an average of these metrics may be calculated. Because novice users will walk more erratically than experienced users, the average will be higher for novice users and lower for experienced users, allowing the controller to quantify the experience of a person. In another embodiment, it is possible for the controller to track the center of pressure of a foot over a stance cycle and fit a curve to the center of pressure trajectory. Then the controller may difference the curve and the actual trajectory and measure the amount of variation of the resulting signal over that step. There are many well understood measurements of the amount of variation of a signal including, as an example, the variance or standard deviation of a signal. It is important to understand that measuring the consistency and smoothness of a signal is well understood in the art and there are many more sophisticated techniques available.

A yet further embodiment can expand any of the described user performance metric generation methods to allow an exoskeleton system to enable and disable states which require differing levels of user proficiency for safe operation. In this embodiment, the exoskeleton system generates a metric for user proficiency directly from the user's operation of the exoskeleton in less advanced safer states as a prerequisite to enable operation of more advanced states requiring greater proficiency to be performed safely. This self-regulating architecture provides the exoskeleton designer with confidence in an unbiased measure of proficiency which provides assurance that states which would be hazardous to a novice exoskeleton user are not inadvertently activated with a novice user. This confidence in the disabling of expert level states with novice user allows the exoskeleton designer to include advanced states that would create too high a liability if included in an exoskeleton device that is not self-regulating.

This metric can also be used to score a physical therapists' competency in operating the exoskeleton. Frequently during training, the physical therapist operator is not sure when the appropriate time to initiate a step is. By providing consistent feedback based on the parameters the operator is being asked to look at, the training process is improved. At the end of training, a score can be determined based on this ideal trigger and the operator in order to determine if they are adequately trained.

This threshold can also be used to score the proficiency of the user. There are numerous measurements relating to the ability to achieve this desired position in preparation for the next step which indicate proficiency in walking. One embodiment is measuring the time from heel strike to the initiation of the next step as the quicker the transition, the more fluid the walking. A second embodiment includes measuring the velocity of the shank angle between heel strike and the initiation of the next step in order to determine fluidity of motion.

Extensions

This method could also be used for additional state determination, such as backwards stepping, sitting and standing. For example, if the shank angle is leaned back sufficiently far, a backwards step would be initiated. This backwards angle indicates a shift in the center of mass backwards and the user will need to step backward in order to support himself. In the case of sitting, if both shank angles are measured sufficiently backwards, the unit can initiate sitting. If both shank angles are leaned forward enough and the joint angles also meet requirements set for safety and balance, the device can initiate standing.

Figure 5:
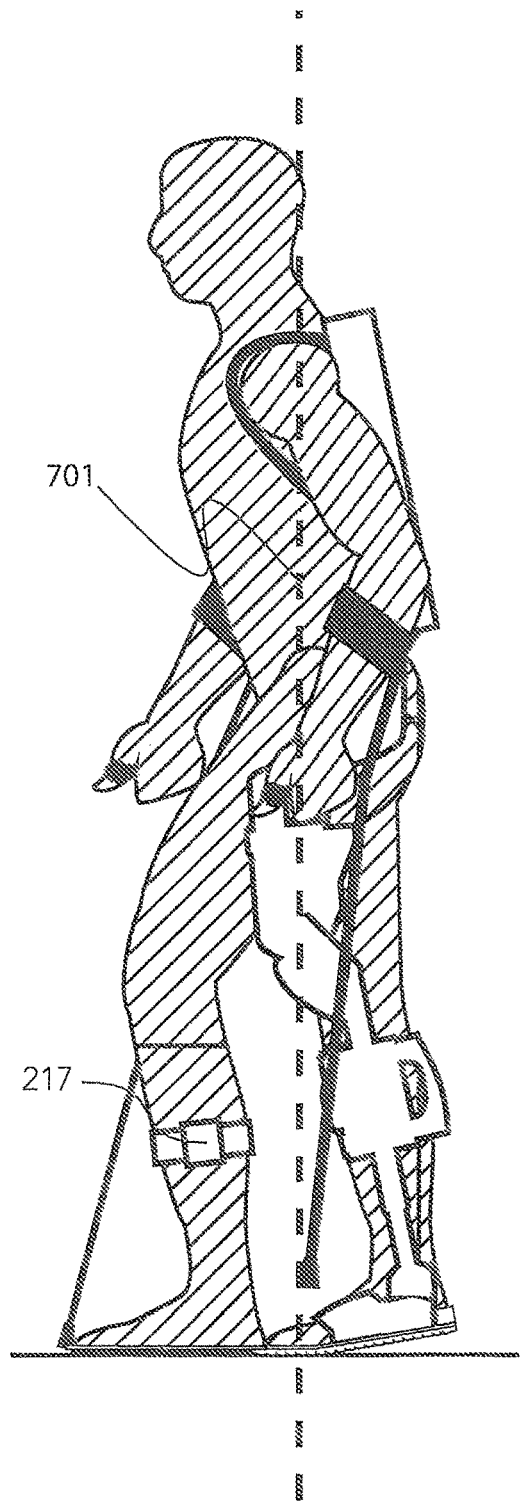
FIG. 5 represents an embodiment with one leg.

In the preferred embodiment, the exoskeleton has two leg supports. However, in some embodiments as shown in FIG. 5, particularly for users who exhibit hemiplegic gait injuries, it may be desirable for the device to have only one leg support. The methods disclosed here use information from one leg to trigger stepping for the other leg; in the event that the device has only one leg support it is possible to obtain the necessary information about the orientation of the lower limb of the person that does not have a leg support (the less affect limb). For example, it would be possible to place a small elastic band on the shank of the less affected limb including an IMU, 217, that would measure the orientation of the shank with respect to the gravity vector (indicated at 701). This information could be relayed wirelessly or with a small cable, to the controller. It is important to understand that all of the techniques disclosed above for the purpose of transitioning a leg into the swing phase apply to a one legged device; it is merely necessary to record the same information from the lower limb of the person with an appropriate set of sensors. For example, it is understood in the art that it is possible to configure a foot force sensor as an insole that fits inside a shoe. As a result, it is possible to relay information about the weight distribution and center of pressure of the person's leg even if the only leg of the device is coupled to the other leg of the person. Furthermore, this same technique could be used if the device is an orthotic that does not extend to the ground but instead ends mid-shank. These examples are meant to be illustrative of the scope of the invention; although a two legged embodiment is primarily discussed, these same techniques may readily be extended to simpler and more minimal devices.

Although described with respect to preferred embodiments of the invention, it should be understood that various changes and/or modifications can be made without departing from the invention. For instance, as a further embodiment, it is possible to measure the moment generated in the ankle of the exoskeleton to estimate the position of the center of pressure in the sagittal plane (this assumes that the person wearing the exoskeleton does not have the ability to generate sagittal plane moments with their ankle). Therefore, it is possible to use measurement of the ankle moment to reliably trigger a step. This embodiment is useful in devices where the ankle of the exoskeleton is stiff or rigid and there may not be suitable motion of the exoskeleton shank for triggering steps. Likewise, if the hip joint is sufficiently rigid during stance, the torque at the hip joint could also be measured to indicate a desire to trigger a step. In general, the invention is only intended to be limited by the scope of the following claims.

We claim:

1. A method of controlling a powered lower extremity orthotic including an exoskeleton having a waist portion configurable to be coupled to an upper body of a person, at least one leg support configurable to be coupled to a first lower limb of the person, at least one actuator for shifting of the at least one leg support relative to the waist portion to enable movement of the first lower limb of the person, and a plurality of sensors for monitoring the exoskeleton, the method comprising:
    monitoring a first orientation of said exoskeleton and a second orientation of a second lower limb of the person;
    regulating operation of the at least one actuator based on the first and second orientations; and
    establishing a present state of said exoskeleton from a finite plurality of states and, based on the present state, controlling the at least one actuator to cause the powered lower extremity orthotic to follow a series of orientations collectively reproducing a natural human motion, wherein the at least one leg support includes a thigh segment rotatably connected to the waist portion and a shank segment rotatably connected to the thigh segment, said method further comprising estimating an angle of the shank segment with respect to vertical, wherein the first orientation is comprised of the angle of the shank segment with respect to vertical, said method further comprising:
    (1) decomposing an absolute angle of the shank segment into a sagittal measurement in the sagittal plane and a coronal measurement in the coronal plane; and placing the at least one leg support corresponding to the first lower limb into a state corresponding to taking a step when the sagittal measurement exceeds at least a sagittal threshold and the coronal measurement exceeds at least a coronal threshold; or
    (2) placing the at least one leg support corresponding to the first lower limb into a state corresponding to taking a step when the angle of the shank segment with respect to vertical exceeds at least a threshold.

2. The method of claim 1, wherein said at least one leg support includes a proximal end rotatably connectable to said waist portion and a distal end, said method further comprising estimating forward and lateral distances from the proximal end to the distal end of said at least one leg support and the first orientation is comprised of said forward and lateral distances from the proximal end to the distal end.

3. The method of claim 1, further comprising estimating an angle of the shank segment with respect to a terrain, wherein the first orientation is comprised of the angle of the shank segment with respect to the terrain.

4. The method of claim 3, further comprising modifying the series of orientations reproducing human motion based on a slope of the terrain.

5. The method of claim 1, further comprising measuring an absolute angle of the shank segment with respect to gravity by means of an inertial measurement unit coupled to the shank segment.

6. The method of claim 1, wherein the first orientation is comprised of three readings constituted by:
    (1) measuring an angular displacement between the shank segment and the thigh segment with an angular displacement sensor;
    (2) measuring the angular displacement between the thigh segment and the waist portion with an angular displacement sensor; and
    (3) measuring the angle of the waist portion with respect to gravity with an inertial measurement unit; and
    estimating the angle of the shank segment with respect to gravity from the three readings.

7. The method of claim 1, wherein said at least one leg support includes a thigh link configured to be coupled to an upper leg of the person and rotatably connected to said waist portion, and said method further comprises measuring an angle of the thigh link with respect to gravity where the first orientation is comprised of said angle of the thigh link.

8. The method of claim 1, wherein the at least one leg support includes a foot configured to rest on a support surface during a stance phase and includes at least one force distribution sensor configured to sense a position of a center of pressure of forces distributed over a bottom of the foot, said method further comprising placing the at least one leg support corresponding to the first lower limb into a state corresponding to taking a step when the center of pressure enters a specified region.

9. A method of controlling a powered lower extremity orthotic including an exoskeleton having a waist portion configurable to be coupled to an upper body of a person, two leg supports configurable to be coupled to lower limbs of the person, and two actuators, one for shifting each leg support relative to the waist portion to enable movement of the lower limb of the person, and a plurality of sensors for monitoring the exoskeleton, the method comprising:
    monitoring a first orientation of said exoskeleton and a second orientation of each of the leg supports;
    regulating operation of the two actuators based on the first and second orientations; and
    establishing a present state of said powered lower extremity orthotic from a finite plurality of states based on both the first and second orientations and, based on the present state, controlling the two actuators to cause the powered lower extremity orthotic to follow a series of orientations collectively reproducing a natural human motion, wherein a first one of the two leg supports includes a foot configured to rest on a support surface during a stance phase and at least one force distribution sensor configured to sense a position of a center of pressure of forces distributed over a bottom of the foot, said method further comprising placing a second one of the two leg supports into a state corresponding to taking a step when the center of pressure enters a specified region.

10. A powered lower extremity orthotic, configurable to be coupled to a person, comprising:
   an exoskeleton including a waist portion configurable to be coupled to an upper body of the person, at least one leg support configurable to be coupled to a first lower limb of the person and at least one actuator for shifting of the at least one leg support relative to the waist portion to enable movement of the first lower limb of the person;
   a plurality of sensors for monitoring a first orientation of said exoskeleton where at least one of the sensors is a leg orientation sensor configured to estimate a second orientation of a second lower limb of the person; and
   a controller configured to receive signals from the plurality of sensors and regulate operation of the at least one actuator, said controller establishing a present state of said powered lower extremity orthotic from a finite plurality of states based on both the first and second orientations and, based on the present state, controlling the at least one actuator to cause the powered lower extremity orthotic to follow a series of orientations collectively reproducing a natural human motion, wherein the at least one leg support includes a thigh segment rotatably connected to the waist portion and a shank segment rotatably connected to the thigh segment, wherein the leg orientation sensor is constituted by an inertial measurement unit coupled to the shank segment and configured to measure an absolute angle of the shank segment with respect to gravity, and wherein:
   (1) the controller is configured to (a) decompose the absolute angle of the shank segment into a sagittal measurement in the sagittal plane and a coronal measurement in the coronal plane and (b) place the at least one leg support corresponding to the first lower limb into a state corresponding to taking a step when the sagittal measurement exceeds at least a sagittal threshold and the coronal measurement exceeds at least a coronal threshold; or
   (2) the controller is configured to place the at least one leg support corresponding to the first lower limb into a state corresponding to taking a step when the absolute angle of the shank segment with respect to gravity exceeds at least a threshold.

11. The powered lower extremity orthotic of claim 10 where the leg orientation sensor includes:
   (1) a first angular displacement sensor configured to measure an angular displacement between the shank segment and the thigh segment;
   (2) a second angular displacement sensor configured to measure an angular displacement between the thigh segment and the waist portion; and
   (3) an inertial measurement unit configured to measure an angle of the waist portion with respect to gravity.

12. The powered lower extremity orthotic of claim 10, wherein the leg support includes a foot configured to rest on a support surface during a stance phase and includes at least one force distribution sensor configured to sense a position of a center of pressure of forces distributed over a bottom of the foot, and wherein the controller is configured to place the leg support corresponding to the first lower limb into a state corresponding to taking a step when the center of pressure enters a specified region.

13. The powered lower extremity orthotic of claim 12, wherein the at least one force distribution sensor includes a heel area sensor configured to sense a force applied to a heel of the foot and a toe area sensor configured to sense a force applied to a toe of the foot.

14. The powered lower extremity orthotic of claim 12, wherein said foot includes an upper side and a lower side, said force distribution sensor including: an elastic housing interlocking with said foot substantially enclosing a perimeter of both the upper and lower sides such that a cavity is formed between the foot and the elastic housing; and an electronic pressure sensor assembly located within the said cavity.

15. The powered lower extremity orthotic of claim 10, wherein the leg support includes a foot configured to rest on a support surface during a stance phase and the foot includes two of the following three sensors:
   (1) a force distribution sensor configured to sense a position of a center of pressure of forces distributed over a bottom of the said foot;
   (2) an interaction torque sensor configured to measure a torque between the leg support and foot; and
   (3) a force distribution sensor configured to sense a position of a center of pressure of forces between the person and the said foot, said controller estimating a measurement of a non-included sensor of the three sensors from the two included sensors.

\* \* \* \* \*